(12) United States Patent
Buschman

(10) Patent No.: US 10,994,141 B2
(45) Date of Patent: May 4, 2021

(54) ADAPTIVE COGNITIVE PROSTHETIC AND APPLICATIONS THEREOF

(71) Applicant: The Trustees of Princeton University, Princeton, NJ (US)

(72) Inventor: Tim Buschman, Haddonfield, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 15/517,331

(22) PCT Filed: Oct. 5, 2015

(86) PCT No.: PCT/US2015/054007
§ 371 (c)(1),
(2) Date: Apr. 6, 2017

(87) PCT Pub. No.: WO2016/057396
PCT Pub. Date: Apr. 14, 2016

(65) Prior Publication Data
US 2017/0304625 A1 Oct. 26, 2017

Related U.S. Application Data

(60) Provisional application No. 62/060,534, filed on Oct. 6, 2014.

(51) Int. Cl.
*A61N 1/36* (2006.01)
*A61B 5/04* (2006.01)
*A61B 5/00* (2006.01)

(52) U.S. Cl.
CPC ...... *A61N 1/36103* (2013.01); *A61B 5/04001* (2013.01); *A61B 5/4064* (2013.01);
(Continued)

(58) Field of Classification Search
CPC .............. A61N 1/3605; A61N 1/36057; A61N 1/3606; A61N 1/36082; A61N 1/36092; A61N 1/36103
See application file for complete search history.

(56) References Cited

U.S. PATENT DOCUMENTS

2002/0103512 A1*  8/2002  Echauz ................ A61B 5/0482
                                                                      607/9
2005/0271277 A1   12/2005  Lin et al.
(Continued)

OTHER PUBLICATIONS

International Search Report and Written Opinion issued in corresponding International Application No. PCT/US2015/054007 dated Jan. 8, 2016.

*Primary Examiner* — Allen Porter
(74) *Attorney, Agent, or Firm* — J. Clinton Wimbish; Nexsen Pruet, PLLC

(57) ABSTRACT

An adaptive cognitive prosthetic that learns to replace neural function that was lost due to a brain injury or disease is described herein. In some embodiments, an adaptive cognitive prosthetic comprises a processing unit for converting input data from an input assembly into a cognitive variable and selecting a stimulation pattern for conveying the cognitive variable. The processing unit employs an adaptive algorithm to assemble the stimulation pattern by combination of subset stimulation patterns, the combination of subset stimulation patterns learned by the adaptive algorithm through error analysis.

14 Claims, 11 Drawing Sheets

Orthogonal Basis for Creating Stimuli: Discrete Cosine Transform

A Low-Frequency Basis Images

B Mixtures of Basis Images Creates Morphs

Morphing towards another basis image

C Heirarchical Construction of Complex Images

'Parent' Stimulus

'Children' Stimuli

(52) U.S. Cl.
CPC .......... *A61B 5/4094* (2013.01); *A61B 5/7264* (2013.01); *A61B 5/7267* (2013.01); *A61N 1/36082* (2013.01); *A61N 1/36139* (2013.01)

(56) References Cited

U.S. PATENT DOCUMENTS

| | | | |
|---|---|---|---|
| 2006/0217781 A1* | 9/2006 | John | G16H 50/50 |
| | | | 607/45 |
| 2010/0036457 A1* | 2/2010 | Sarpeshkar | A61N 1/36046 |
| | | | 607/53 |
| 2011/0001924 A1 | 1/2011 | Giraudet et al. | |
| 2011/0004072 A1 | 1/2011 | Fletcher et al. | |
| 2013/0060266 A1 | 3/2013 | Bretthauer et al. | |
| 2013/0090535 A1 | 4/2013 | Hegg et al. | |
| 2013/0218819 A1 | 8/2013 | Lujan et al. | |
| 2014/0180361 A1 | 6/2014 | Burdick et al. | |

* cited by examiner

FIGURE 7

ADAPTIVE COGNITIVE PROSTHETIC AND APPLICATIONS THEREOF

RELATED APPLICATION DATA

This application is a U.S. National Phase of PCT/US2015/054007, filed Oct. 5, 2015, which claims priority under 35 U.S.C. § 119(e) to U.S. Provisional Patent Application Ser. No. 62/060,534 filed Oct. 6, 2014, each of which are incorporated herein by reference in their entireties.

STATEMENT OF GOVERNMENT RIGHTS

This invention was made with government support under Grant No. 1DP2EY025446 awarded by the National Institutes of Health. The government has certain rights in the invention.

FIELD

The present invention relates to prosthetics for alleviating various neurological and/or neuropsychiatric disorders and, in particular, to adaptive cognitive prosthetics capable of learning to replace or augment function lost by a damaged or diseased brain region.

BACKGROUND

Traumatic brain injuries and various neurological diseases severely reduce the quality of life for affected individuals and carry significant societal and economic costs. For example, every year over 600,000 individuals in the United States experience a stroke according to Center for Disease Control (CDC) estimates. Further, the CDC estimates over 275,000 individuals suffer traumatic head injuries requiring hospitalization. In many cases, individuals never fully recover from these injuries and exhibit limited function due to one or more cognitive disabilities.

SUMMARY

In one aspect, adaptive prosthetics are described herein which, in some embodiments, can restore cognitive function lost or impaired by a damaged or diseased brain region. For example, an adaptive cognitive prosthetic comprises a processing unit for converting input data from an input data assembly into a cognitive variable and selecting a stimulation pattern for conveying the cognitive variable. As described further herein, the cognitive variable corresponds to the computational function managed by the damaged region of the brain being replaced or by-passed by the adaptive cognitive prosthetic. Importantly, the processing unit employs an adaptive algorithm to assemble the stimulation pattern by combination of subset stimulation patterns, the combination of subset stimulation patterns learned by the adaptive algorithm through error analysis. In some embodiments, for example, the adaptive algorithm is a hierarchical learning algorithm. A stimulation assembly of the cognitive prosthetic administers the selected stimulation pattern.

In another aspect, methods of providing stimulation patterns for conveying cognitive variables are described herein. Such methods, in some embodiments, comprise providing input data to a processing unit from an input data assembly and converting the input data into a cognitive variable with the processing unit. A stimulation pattern for conveying the cognitive variable is selected by the processing unit, wherein the processing unit employs an adaptive algorithm to assemble the stimulation pattern by combination of subset stimulation patterns, the combination of subset stimulation patterns learned by the adaptive algorithm through error analysis. As described further herein, the subset stimulation patterns can be assembled in a hierarchical format. A stimulation assembly of the cognitive prosthetic administers the selected stimulation pattern.

These and other embodiments are described in greater detail in the detail description which follows.

BRIEF DESCRIPTION OF THE DRAWINGS

FIG. 7 illustrates performance of a patient with hemispatial neglect on a visual search task.

DETAILED DESCRIPTION

Embodiments described herein can be understood more readily by reference to the following detailed description and examples and their previous and following descriptions. Elements and apparatus described herein, however, are not limited to the specific embodiments presented in the detailed description. It should be recognized that these embodiments are merely illustrative of the principles of the present invention. Numerous modifications and adaptations will be readily apparent to those of skill in the art without departing from the spirit and scope of the invention.

An adaptive cognitive prosthetic described herein comprises a processing unit for converting input data from an input data assembly into a cognitive variable and selecting a stimulation pattern for conveying the cognitive variable.

The processing unit employs an adaptive algorithm to assemble the stimulation pattern by combination of subset stimulation patterns, the subset stimulation patterns learned by the adaptive algorithm through error analysis.

Turning now to specific components, the adaptive cognitive prosthetic measures/collects input data with an input data assembly. Types of input data can vary according to the identity of the cognitive variable of interest. In some embodiments, input data comprises environmental stimuli such as electromagnetic radiation, heat, sound, tactile sensation(s), chemosensation(s) and/or sensations of movement, such as gravity or acceleration forces. Such environmental stimuli can be measured and collected with a variety of detection apparatus including focal plane arrays, charge coupled devices, photodiode arrays, thermometers, thermocouples, chemosensors, tactile sensors and/or accelerometers.

Figure 1:
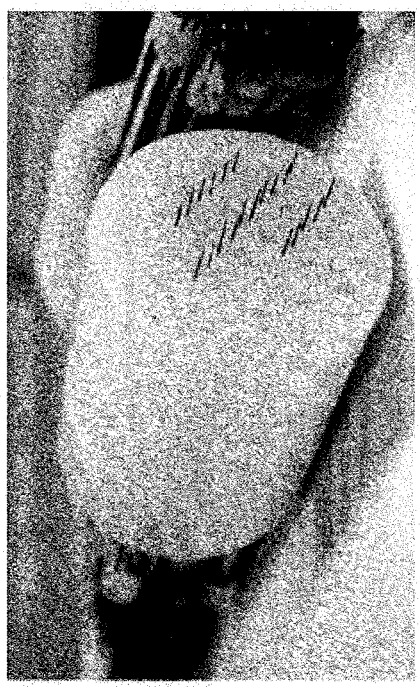
FIG. 1 illustrates an electrode assembly operable for recording and/or stimulating neural activity across several brain regions according to one embodiment described herein.

Collected input data can also include neural activity from a patient. Neural activity of a patient can be measured and collected by a variety of techniques. For example, fluctuations in electric potential from a single neuron or a population of neurons can be measured using electrodes in contact with the brain or positioned outside the skull. Generally, invasive microelectrodes can be employed for monitoring single neuron activity or electroencephalography (EEG) electrodes are placed on the scalp to record population activity. FIG. 1 illustrates an electrode assembly operable for recording neural activity across several brain regions according to one embodiment described herein.

Alternatively, magnetic field fluctuations resulting from current flow in the brain can be measured. Neural activity can also be measured by one or more chemical techniques including variances in ion concentrations such as sodium, potassium and/or calcium. In further embodiments, neural activity can be ascertained by the measuring the concentration of neurotransmitters, gene expression and/or metabolites. Functional magnetic resonance imaging (fMRI) using blood-oxygen-level dependent (BOLD) contrast, in some embodiments, is used to quantify neural activity. The measured neural activity can correspond to responses to environmental stimuli encountered by the patient. The measured neural activity may also originate from self-generated thought(s) or desire(s) of a patient, such as thoughts to begin or desist a specific behavior.

Physiological signals from the body can also serve as input data for the adaptive cognitive prosthetic.

The input data is converted into a cognitive variable by a processing unit of the adaptive cognitive prosthetic. For example, input data in the format of an image of a patient's environment is converted to a cognitive variable serving to differentiate objects in the environment. As part of the differentiation, the cognitive variable may rank objects in the imaged environment according to various criteria, such as interest of the object to the patient. As described above, the input data of the image may be provided by a focal plane array and associated electronics. Alternatively, the input data may be neural activity in the visual cortex that carries information regarding the image of the environment.

The processing unit can also select a stimulation pattern for conveying the cognitive variable. As described herein, the processing unit can employ an adaptive algorithm to assemble the stimulation pattern by combination of subset stimulation patterns, the combination of subset stimulation patterns learned by the adaptive algorithm through error analysis. Various adaptive algorithms can be used to learn and select the appropriate stimulation pattern. The adaptive algorithm, in some embodiments, can learn and select stimulation patterns unique to each cognitive variable encountered. High-dimensionality is important for the adaptive cognitive prosthetic. High dimensionality provides diversity of outputs required to match everyday experiences.

In some embodiments, the adaptive algorithm employs a hierarchical learning algorithm. In such embodiments, subset stimulation patterns are combined in a hierarchical format. For example, subset stimulation patterns can be combined in order of increasing complexity. Subset stimulation patterns conveying basic functions or characteristics of the cognitive variable can be combined first, followed by the addition of subset stimulation patterns of increasing complexity for conveying more intricate functions or characteristics of the cognitive variable. As detailed further herein, the adaptive algorithm can employ a continuous error function for evaluating the accuracy of each combination of subset stimulation patterns for conveying one or more functions or characteristics of the cognitive variable. If a combination of subset stimulation patterns does not meet a set accuracy threshold, the combination is discarded. In this way, the adaptive algorithm learns the combination of subset stimulation patterns for accurately conveying the cognitive variable. Evaluation of whether a combination of subset stimulation patterns meets a set or predetermined accuracy threshold can be guided by feedback from a behavioral paradigm and/or directly from the patient using the adaptive cognitive prosthetic. Feedback from the behavioral paradigm can vary, including non-limiting metrics listed in Table I.

TABLE I

Behavioral Paradigm Metrics

Simple success/failure feedback on every trial of subset stimulation pattern combination (e.g. patient correctly identified a tone or found a target stimulus in a visual search
Graded responses from the patient to provide detailed error signals to the learning algorithm (e.g. patient identified a tone has having a frequency of X kHz which was off by Y kHz)
Time required for patient to perform a task
Scores that encapsulate several aspects of performance on a behavioral task (e.g. how many targets were found in a visual search display with bonus factors for faster performance)

Feedback from the patient can also vary, including the non-limiting metrics provided in Table II.

TABLE II

Patient Feedback Metrics

Closeness of elicited neural activity with a predetermined desired pattern. This can include several metrics (e.g. Mahalanobis distance, discriminability, etc.) acting on either a single neuron activity or the activity of populations of neurons and either within a single brain region or across several regions; changes in temporal patterning, such as synchronous oscillations, can be included.
Changes in concentrations of neurotransmitters, neuromodulators or ions
Changes in gene expression
Changes in systemic physiological values (e.g. heart rate, blood sugar, hormone levels, etc.)

Any combination of the metrics of Tables I and II can be used in the continuous error function. Further, the feedback can vary at different points during learning.

Importantly, learning by assembling the stimulation pattern from a combination of subset patterns significantly reduces computational complexity while providing high dimensionality. As described above, subset stimulation patterns conveying basic functions or characteristics of the cognitive variable are learned first by the adaptive algorithm. Once sufficient accuracy is reached, subset stimulation patterns of increasing complexity are added for conveying more intricate functions or characteristics of the cognitive variable. Such hierarchical assembling permits the facile evaluation of numerous subset pattern combinations yielding a highly effective stimulation pattern for conveying the cognitive variable.

Figure 2:
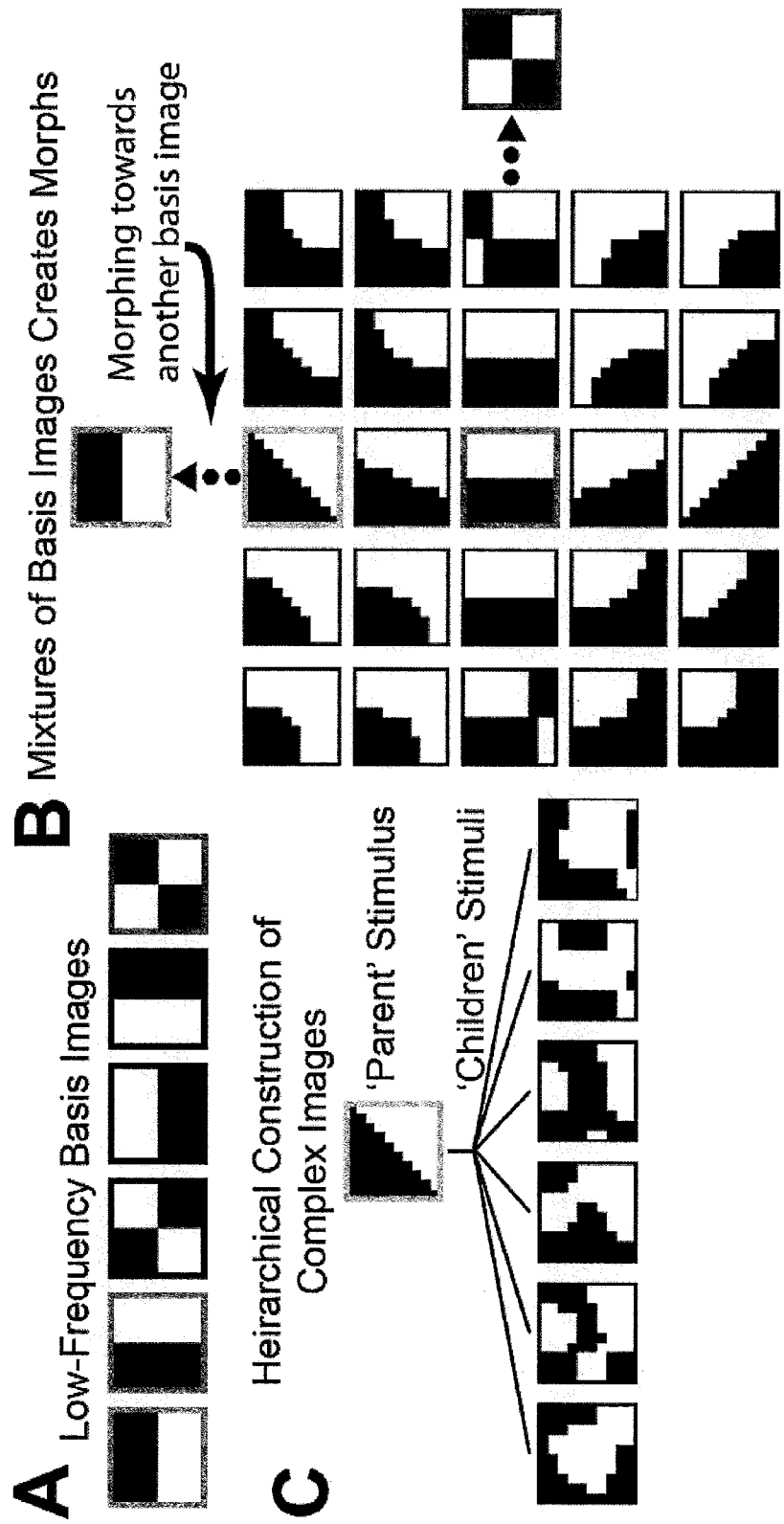
FIGS. 2A-C illustrates a hierarchical learning algorithm according to one embodiment described herein.

As an example, stimulation patterns for conveying cognitive variables can be constructed from discrete cosine transforms (DCTs). With reference to FIG. 2, DCTs have two properties crucial for the learning algorithm. First, DCTs provide a continuous space for generating stimuli. In other words, one can continuously combine multiple subset stimulation patterns to generate 'morphed' images that vary smoothly in space (see FIG. 2B for an example). The continuous nature of DCTs allows the learning algorithm to assume a continuous error function, improving performance.

Second, DCTs meet hierarchical requirements described above: low-frequency basis functions can be used to broadly estimate low complexity subset stimulation patterns (FIG. 2A) which then become refined with the addition of higher-frequency basis functions representing higher complexity subset stimulation patterns. (FIG. 2C). Such hierarchy is crucial to the learning algorithm: it effectively reduces the dimensionality of the stimulation patterns being estimated at any point in time. The algorithm can first learn the optimal combination of the low-frequency images shown in FIG. 2A (example mixtures are seen in FIG. 2B). After learning has plateaued, these lower-frequency components can be fixed (or learning slowed) and the next level of higher-frequency components can be learned (these 'children' stimuli are seen in FIG. 2C and are also continuous). In this way learning is limited to a subset of parameters at a time, reducing the high-dimensional search space, and allowing for effective learning to take place.

Alternatively, stimulation pattern space can be divided using a series to convergently approximate a function. Suitable convergent series can include the Taylor series, Volterra series and Fourier series. The Taylor series, for example, permits any locally differentiable function to be approximated by a summation of weighted polynomials. The polynomials become a basis set from which any function can be constructed. Generally, parameters for polynomials of increasing order (e.g. linear, then quadratic, cubic, etc.) would be estimated, thereby retaining the hierarchical assembly provided by the adaptive algorithm.

Once the appropriate stimulation pattern is learned and selected, a stimulation assembly is employed to administer the selection pattern to one or more intact regions of the brain. Any stimulation assembly not inconsistent with the objectives of the present invention can be used. In some embodiments, the stimulation assembly comprises multiple 3-D waveguides for light-based stimulation. Such waveguides can use genetically-encoded light-sensitive ion channels to manipulate neural activity with light. Activation of these channels is extremely rapid, allowing neural activity to be controlled with millisecond precision. Typically, neuron activity is controlled by laser light that is channeled into the brain with fiber optics. However, the spatial precision of this approach is coarser than the spatial resolution of neurons (~1 mm). Therefore, 3D optogenetic stimulation arrays that deliver light with 100 micron precision can be used. (FIG. 3).

Figure 3A:
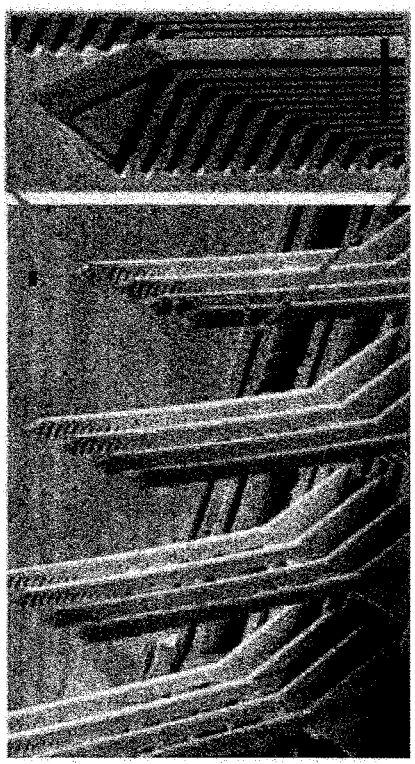
FIGS. 3A-C illustrate optical waveguides and apparatus for administering selected stimulation patterns according to one embodiment described herein.
Figure 3B:
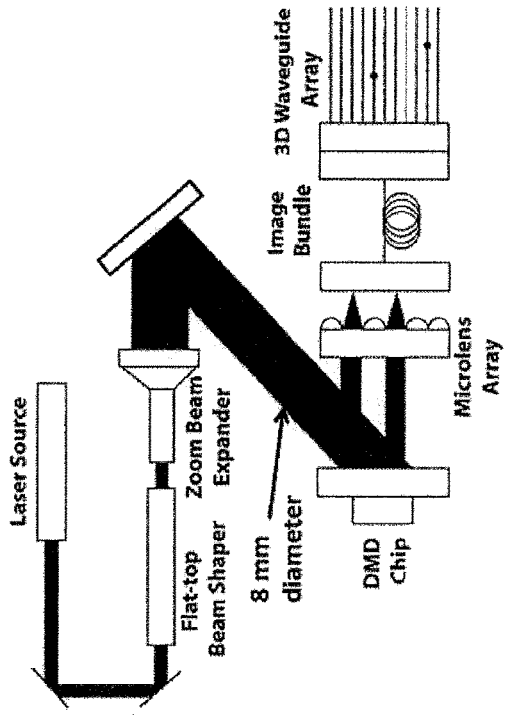
Figure 3C:
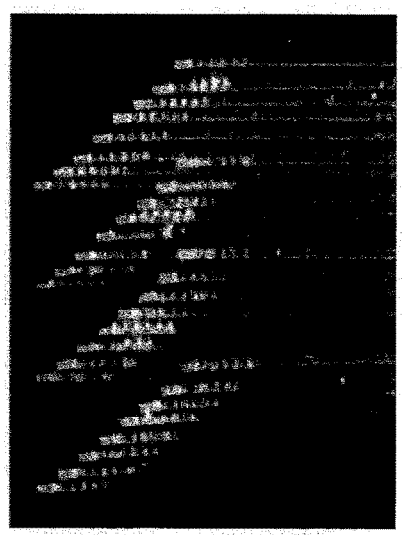

To achieve this precision, the arrays are micro-fabricated on silicon wafers, much like electronic circuit boards. However, instead of gold wires carrying electrical signals, silica waveguides guide light into the brain. Several waveguides can be placed in parallel, running along a sharpened 'shank' that can pierce neural tissue (FIG. 3A, magnified area). By adjoining several of these shanks in the horizontal plane perpendicular to the shank, a 3D array can be constructed (FIG. 3A). The waveguides carry light from the flat back-end of the array into the brain. Therefore, delivering a 2D pattern of light onto the back of the array will lead to a 3D pattern of light in the brain. FIG. 3B shows one approach to creating such a pattern: a high-powered laser is reflected off a digital micro-mirror device (DMD) into the 3D array. DMDs consist of over a million miniature mirrors that, when 'ON', direct laser light into the 3D array (and when 'OFF' direct it away from the array). In this way, we can pattern the orientation of the micro-mirrors in order to create a 3D pattern of light in the brain (FIG. 3C). Furthermore, we maintain the temporal accuracy of optogenetics—DMDs can update at rates well over 1 kHz.

Alternatively, the stimulation assembly can comprise an array of electrodes for administering the selected stimulation pattern via electrical current. In some embodiments, the stimulation assembly employs heating elements for administering the selected stimulation pattern via thermal stimulation. In some embodiments, the stimulation assembly employs a transducer array for mechanically administering the selected stimulation pattern through ultrasound. In further embodiments, the stimulation assembly administers the selected stimulation pattern via fluctuating magnetic fields.

In another aspect, methods of providing stimulation patterns for conveying cognitive variables are described herein. Such methods, in some embodiments, comprise providing input data to a processing unit from an input data assembly and converting the input data into a cognitive variable with the processing unit. A stimulation pattern for conveying the cognitive variable is selected by the processing unit, wherein the processing unit employs an adaptive algorithm to assemble the stimulation pattern by combination of subset stimulation patterns, the combination of subset stimulation patterns learned by the adaptive algorithm through error analysis as described hereinabove. The subset stimulation patterns can be assembled in a hierarchical format. A stimulation assembly of the cognitive prosthetic administers the selected stimulation pattern. Components of methods described herein, including input data, processing unit and stimulation assembly can have construction and/or properties recited above. Further, stimulation patterns of the methods can be assembled according to the learning principles described above governing the hierarchical adaptive algorithm.

These and other aspects are further illustrated by the following non-limiting examples.

Example 1—Adaptive Learning Algorithm and Dimensionality Reduction

Initially, a 'random walk' model was tested to learn appropriate stimulation patterns. The random walk did not reduce dimensionality when attempting to learn the appropriate stimulation patterns. Two different methods of reducing dimensionality of the learning problem were then tested: (1) DCT (a frequency based method discussed herein, similar to Fourier transform) and (2) a sequential subspace (learning on local subsets of neurons at a time). Importantly, since all three methods used the same learning algorithm, the only difference was whether leaning occurred in a structure subspace (e.g. reduced dimensionality, either based on DCT or sequential) or leaning was conducted over the entire space (random walk).

Figure 4:
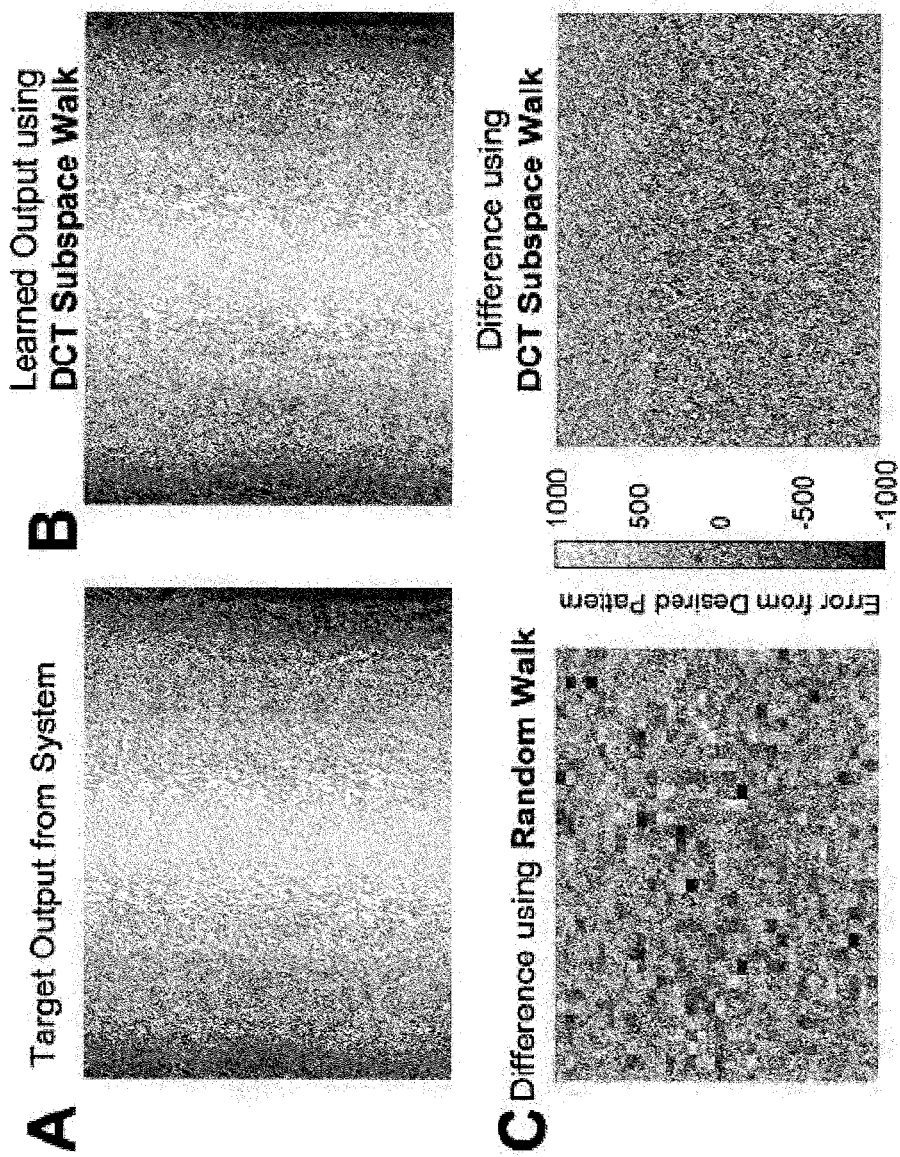
FIG. 4(A) illustrates a target output from an adaptive cognitive prosthetic.
FIG. 4(B) illustrates an output of the adaptive cognitive prosthetic learned by reducing dimensionality via discrete cosine transform (DCT) according to some embodiments described herein.
FIG. 4(C) illustrates error between the target output of an adaptive cognitive prosthetic and outputs determined by random walk and DCT according to some embodiments described herein.

Using reduced dimensionality, the learning algorithm was able to effectively learn what stimulation patterns generated a target response from the neural network model employed in this Example 1. FIG. 4(A) shows the desired stimulation pattern output while FIG. 4(B) shows the learned response stimulation pattern using the DCT subspace approach. The error between the target output and the generated response was calculated by directly subtracting the two patterns. FIG. 4(C) illustrates this error was significantly reduced when using the DCT subspace (right) in comparison with the default random walk (left).

Figure 5:
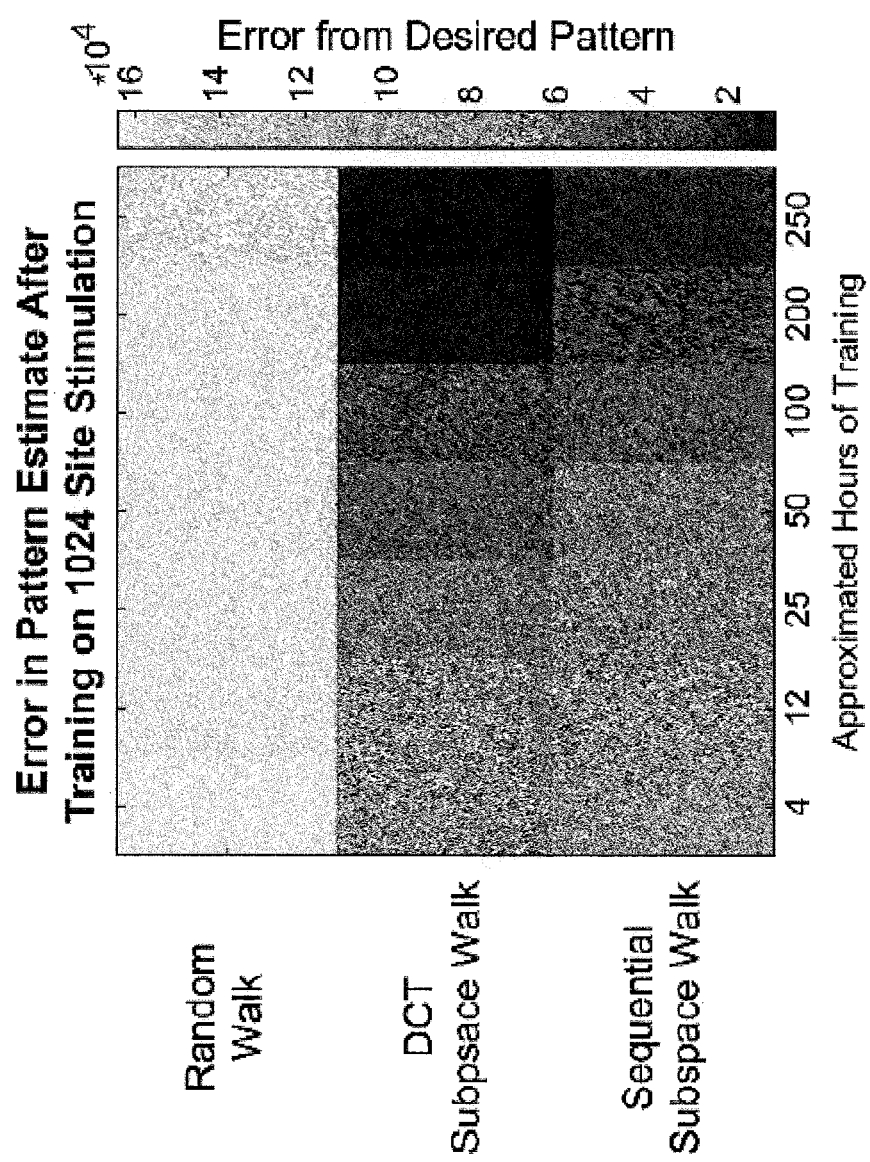
FIG. 5 illustrates stimulation pattern learning rate according to three subspace approaches described herein.

A key aspect of the adaptive cognitive prosthetic described herein is that the prosthetic learns on a limited number of iterations. Assuming behavioral tasks can be completed at a rate of about 4 trials per minute, this limits the algorithm to about 60,000 iterations in 250 hours (i.e. in about 1 year). FIG. 5 illustrates the relative speed of learning for the three approaches of this Example 1. For the localized structure of the cortex, the DCT is highly effective and able to learn significantly faster than the random walk and sequential subspace. With only 4 hours of training, the DCT drastically reduced error between the target stimulation pattern and learned stimulation pattern.

Figure 6:
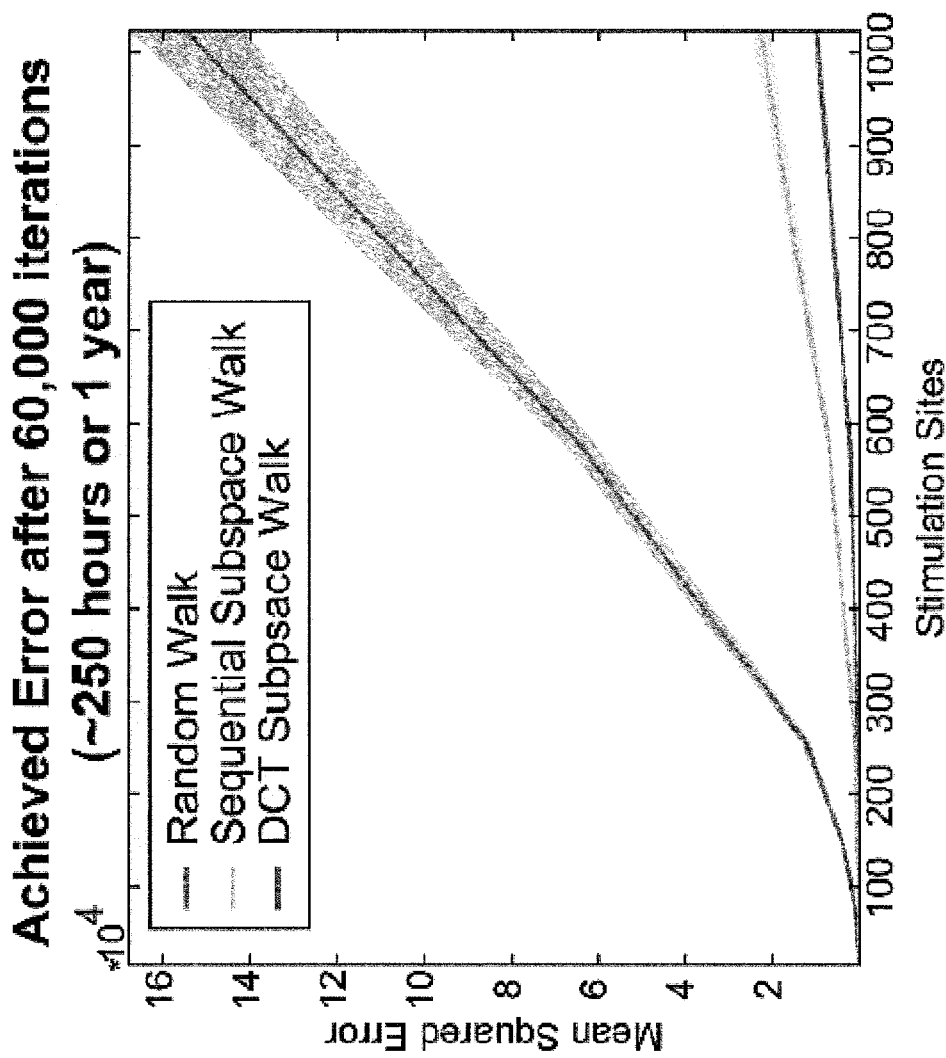
FIG. 6 illustrates the relationship between stimulation pattern error and number of stimulation sites for three learning algorithm approaches described herein.

In addition to learning rapidly, the adaptive cognitive prosthetic must learn simulation patterns in high-dimensional space. The need to stimulate at many sites exacerbates the leaning problem, as illustrated in FIG. 6. Increasing the number of stimulation sites causes an exponential increase in learning error using the default random walk algorithm; learning in subspaces as described herein renders high-dimensional stimulation feasible.

Example 2—Hemispatial Neglect Following Parietal Cortex Stroke

Hemispatial neglect is a common symptom following damage to the right posterior parietal cortex. Patients with hemispatial neglect show a characteristic decrease in awareness of objects in their contralesional visual field (i.e. objects on the left of patients with right parietal damage). This can dramatically impact their everyday lives, causing them to ignore objects in the affected part of the visual field. This deficit extends beyond simple perception—memory and actions towards the affected side are also reduced. For example, patients with hemispatial neglect will often neglect to care for the contralesional side of their body (e.g. only shaving the right half of their face).

Figure 7:
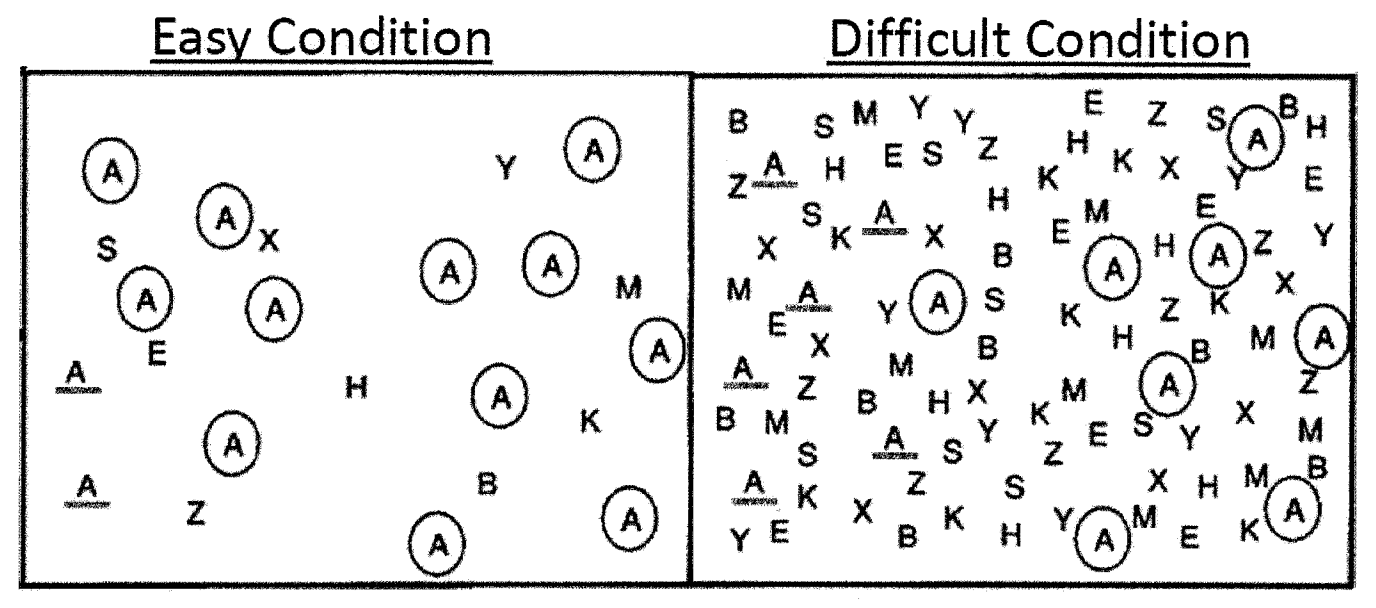

Because lesions associated with hemispatial neglect are relatively common, its behavioral deficits have been well characterized. Under systematic study it was found that neglect only occurs in crowded visual scenes. For example, FIG. 7 shows the performance of patients performing a visual search task (to find all of the 'A's). Patients can perform this task well when the targets are presented with only a few distractors (FIG. 7, left; black circles indicate targets the patient found, black underlines are missed targets), demonstrating they do not have difficulty perceiving them. However, they are no longer able to locate the target stimuli in the affected (left) hemifield when the visual scene becomes cluttered with distractors (FIG. 7, right). This impairment does not extend to the unaffected (right) side.

These results highlight the difficulty stroke patients with hemispatial neglect have in selecting behaviorally relevant stimuli in the affected visual hemifield. Such behavioral deficits led to the theory that parietal cortex is involved in directing attention: when parietal cortex is lost, patients simply cannot attend to stimuli in the contralateral hemifield, making it difficult to perceive individual items in a crowded visual scene. Work in non-human primates has helped to shed light on the exact role of parietal cortex in visual perception and the control of attention.

Figure 8:
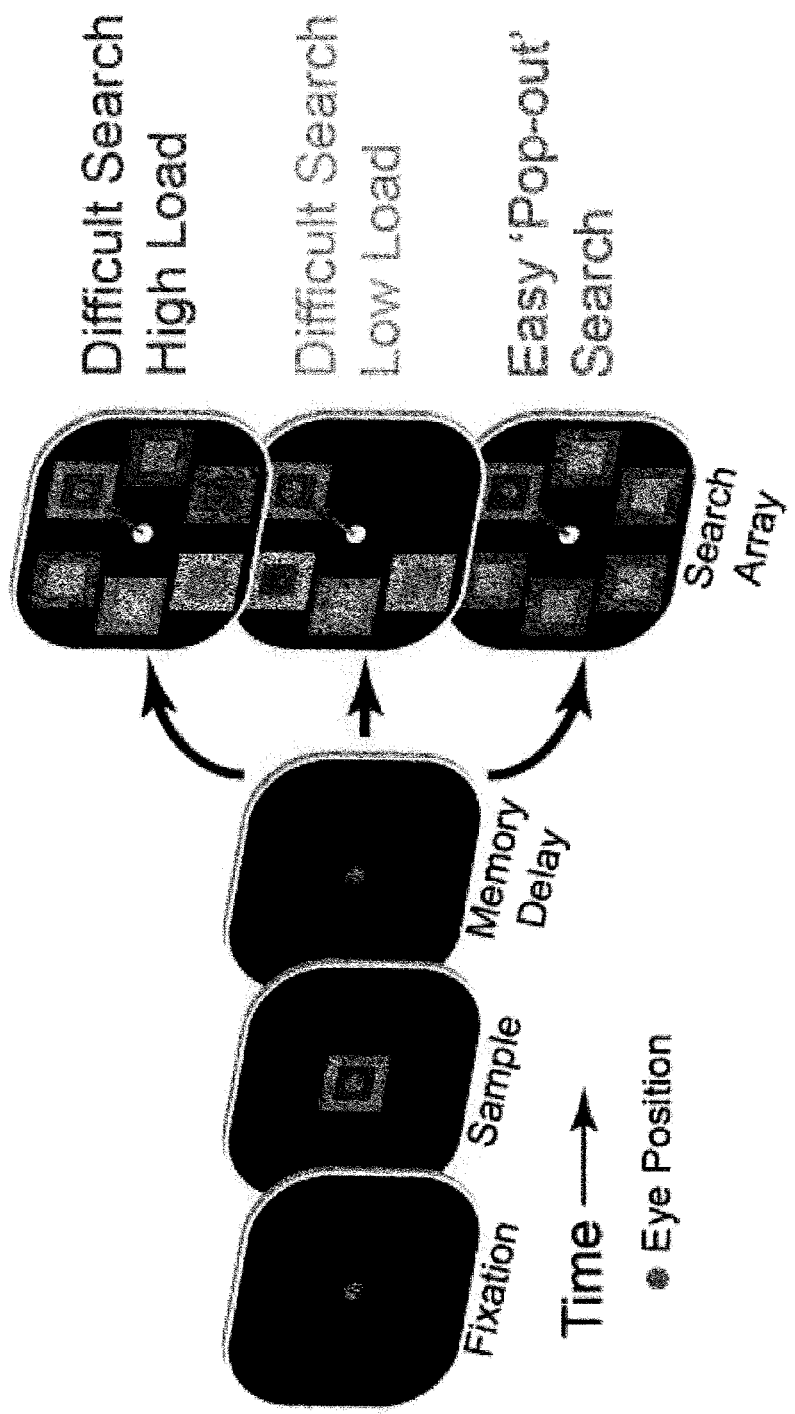
FIG. 8 illustrates a visual search task used in understanding the role of frontal and parietal cortex in internal and external control of attention.
Figure 9:
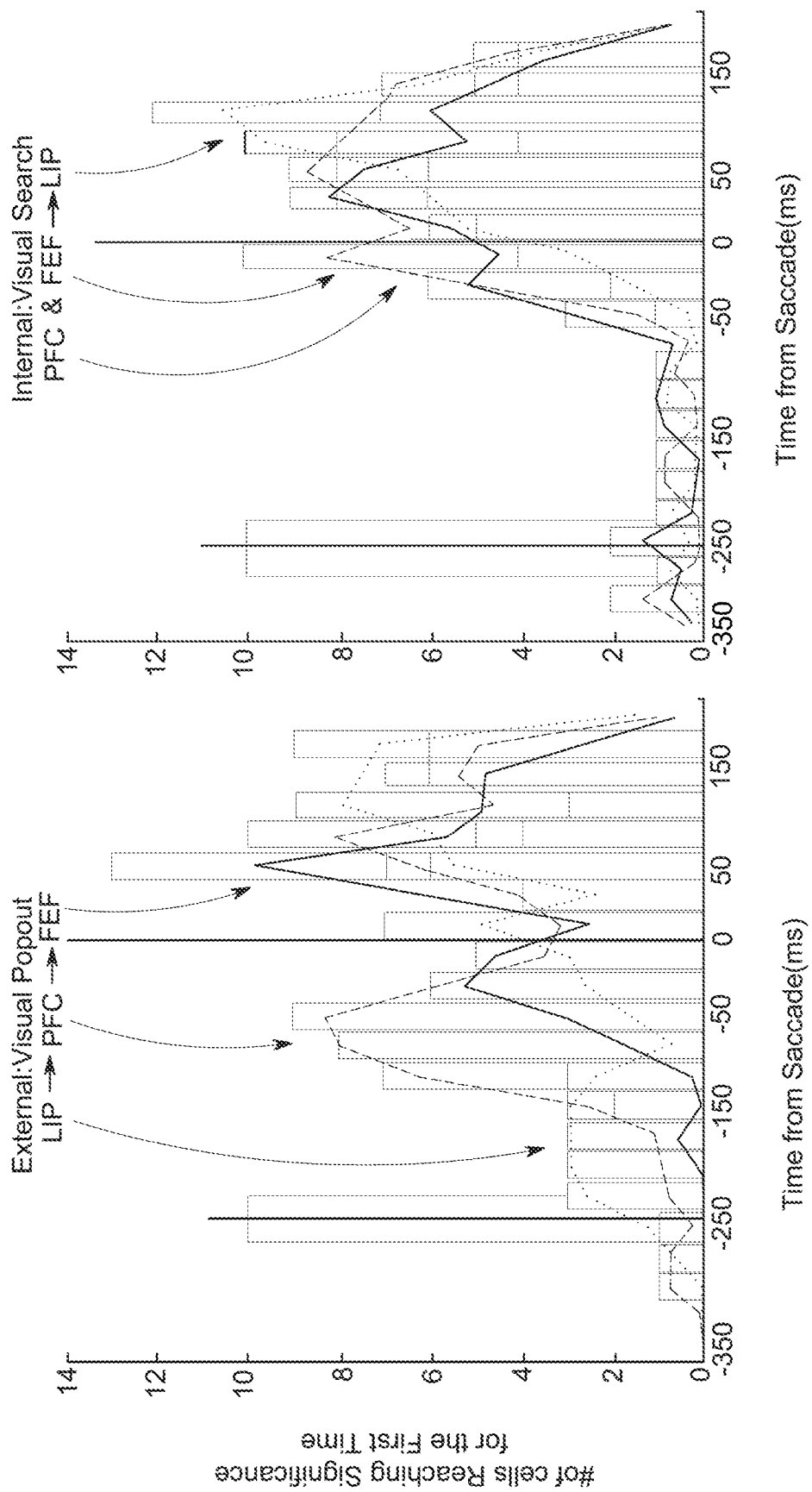
FIG. 9 illustrates the time course of neural selectivity when attention is either externally captured by salient stimulus (left) or internally directed (right).

Two monkeys were trained to find a visual target under difficult and easy search conditions (as in the top and bottom rows of FIG. 8). To understand the role of frontal and parietal cortex in these two forms of attention, 70-100 neurons across both regions were simultaneously recorded. It was then determined when each neuron first reflected attention to the target location. During easy search, when attention was externally grabbed, parietal (LIP) neurons found the target first, followed by prefrontal neurons (PFC and then FEF; FIG. 9, left). By contrast, during a difficult search that required internal control of attention, neurons found the target in the reverse order: the frontal areas (PFC and FEF) showed selectivity first, followed by parietal (LIP; FIG. 9, right). This study provided the earliest direct evidence that internal, willful, control of attention originates in frontal cortex.

In addition, the study provided evidence that parietal cortex (LIP) plays a leading role when attention is captured by a salient external stimulus (FIG. 9, left). As noted above, salience is an integration of bottom-up and top-down biases: brighter and faster-moving stimuli are always salient, regardless of task (bottom-up) while stimuli that share an attribute of the searched-for target can be salient in a particular task (top-down, e.g. green vegetables in a produce stand when looking for an apple). Neurons in parietal cortex integrate bottom-up and top-down biases to encode the saliency of a visual object. Competition between the representation of multiple objects gives rise to a 'priority' map where the most salient object is strongly represented. This priority map can then drive attention—one should attend to the highest priority object at any moment When parietal cortex is damaged this priority map can be disrupted. Indeed, this fits the behavioral deficits observed in hemispatial neglect: if objects in the contralesional (affected) hemifield are no longer able to 'compete' for representation in the saliency map then they will be ignored. This is particularly true for cluttered displays where many objects are competing for representation. Indeed, monkeys with a lesion in parietal cortex (LIP) are not impaired in finding targets when presented alone but have difficulty performing difficult visual search tasks. This not only supports the hypothesis that parietal cortex (LIP) carries a saliency map of the visual scene but also demonstrates lesions to parietal cortex in non-human primates is a good model system for hemispatial neglect in human patients.

In order to effectively replace a damaged brain region, its computational function must be emulated. This is a three-step process. First, inputs from many-electrode recordings must be parsed. Second, these inputs must be transformed to a cognitive variable according to the computation of the to-be-replaced region. As the aim of this Example is to replace a damaged parietal cortex, the adaptive cognitive prosthetic must transform visual inputs into a saliency map (the internal cognitive variable thought to be computed in LIP, as detailed above). Finally, the resulting cognitive variable must be conveyed to intact brain regions via stimulation. However, what stimulation pattern best conveys the cognitive variable is unknown and must be learned. An outline how the adaptive algorithm performs each of these three steps is briefly provided.

Parsing of neural inputs is done online and in real-time. Band-pass filtering of the raw voltage signal from electrodes of the recording assembly separate the low-frequency local field potential (LFP) and the high-frequency signal containing the action potentials from individual neurons. LFPs provide a measure of the local neural population and carry information in their spectral content—for example, visual stimuli induce strong gamma-band (45-90 Hz) oscillations in the LFP of visual cortex. The action potentials of neurons will be isolated from the high-frequency signal using a custom algorithm developed on >2,000 previously recorded (and sorted) neurons. The resulting multi-unit activity (MUA) is ideal for a cognitive prosthetic: it approximates the spatio-temporal precision of single neuron activity while being more robust to noise and electrode drift. Together, the LFP and MUA will provide the neural inputs into the algorithm.

Figure 10:
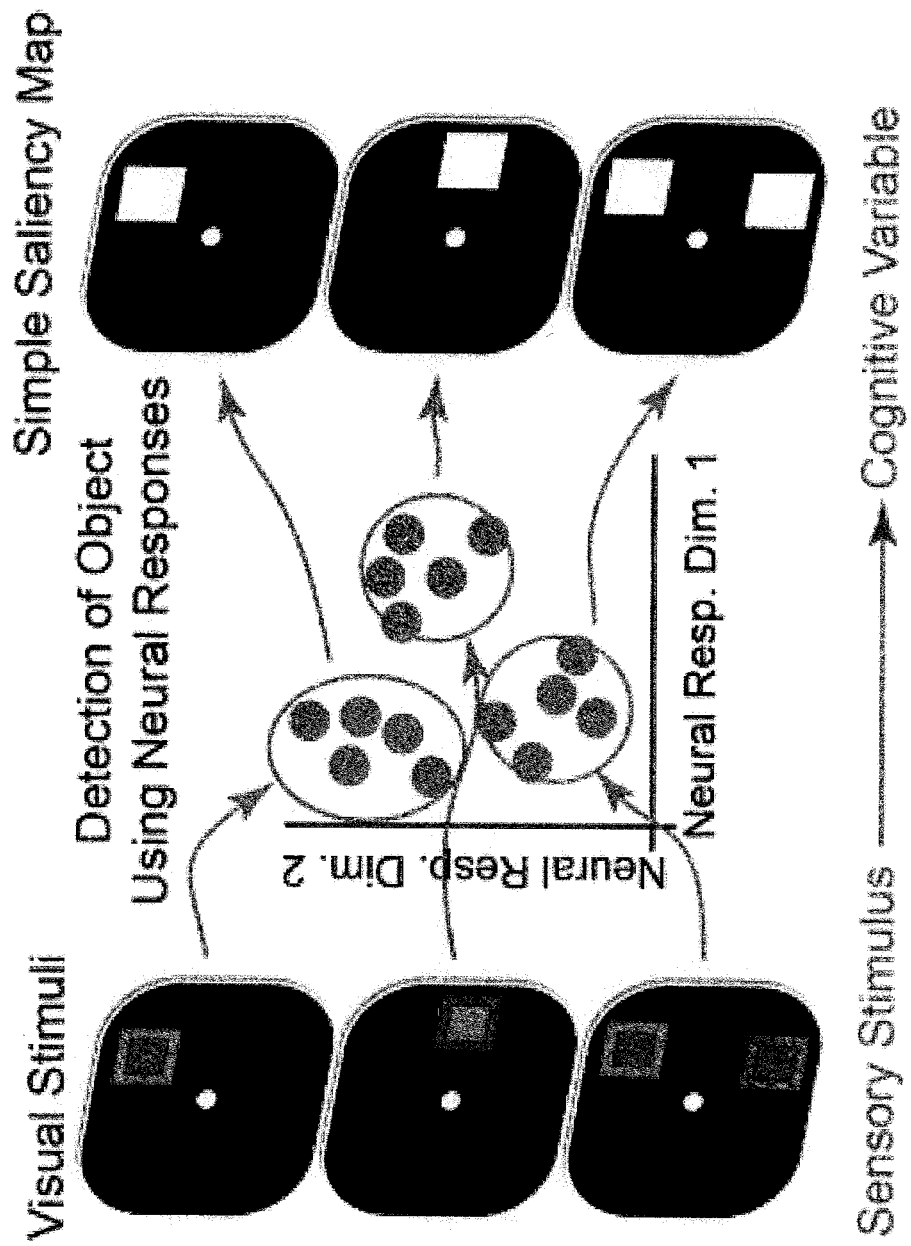
FIG. 10 illustrates transformation from sensory stimulus (unobserved) to neural activity (observed) to a simple saliency map, approximating the cognitive variable of LIP according to one embodiment described herein.

For the initial adaptive prosthetic, the simplest form of a saliency map is determined: one that encodes whether a stimulus exists, without encoding its relative saliency to other objects in the scene (FIG. 10). Recorded neural activity in visual cortex detects whether there is an object at each possible location. Detection of the visual array is accomplished with a simple classification algorithm on all simultaneously recorded neural signals in visual cortex (i.e. both LFP and MUA in V4 and IT). First, these signals are projected into a lower-dimensional space that captures the majority of signal variance (e.g. through principal component analysis, FIG. 10, middle). Then, classification is done via k-means clustering to determine what stimuli are visible (FIG. 10, middle). This is then used to construct a 'flat' saliency map that reflects the location of stimuli (FIG. 10, right). Improvements to the saliency map to encode relative saliency by integrating 'bottom-up' signals recorded from neurons in visual cortex and 'top-down' signals recorded from neurons in prefrontal cortex are also achieved.

Once categorized, each saliency map must be transformed into a unique pattern of stimulation. However, the 'correct' stimulation pattern is unknown and, therefore, must be learned. And so, the adaptive cognitive prosthetic uses a learning algorithm that minimizes an error function defined by behavioral performance: the cognitive prosthetic is performing well when behavioral performance is high. In other words, the algorithm finds stimulation patterns unique to each cognitive variable (in this case, saliency maps) that improves behavioral performance to the greatest degree.

Figure 11:
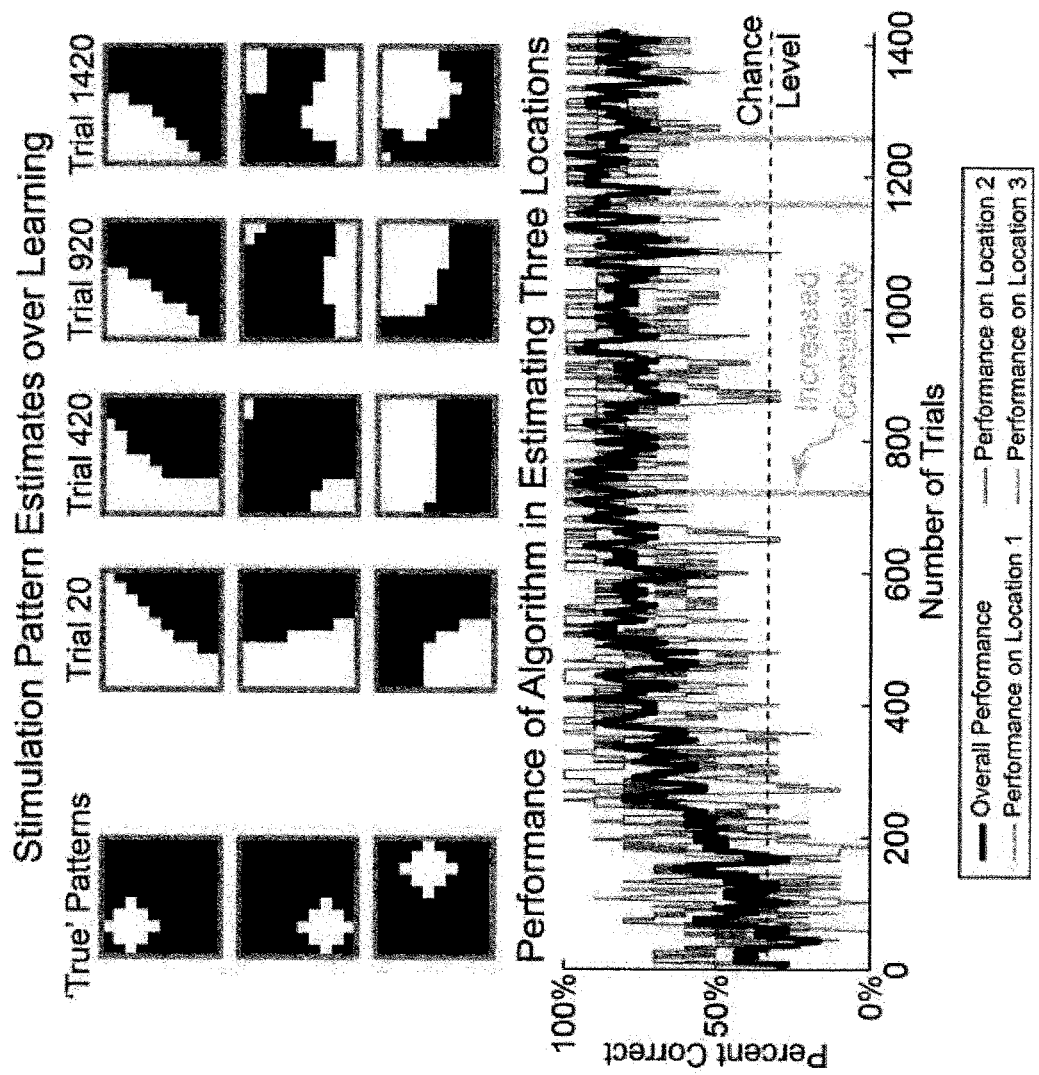
FIG. 11 illustrates a computational test of an adaptive cognitive prosthetic according to one embodiment described herein.

However, this process is made difficult by the high-dimensionality of the possible stimulation patterns (theoretically up to $2^{200}$ unique patterns for a 200-site stimulator). To address this, a DCT is employed as the hierarchical learning algorithm as discussed in relation to FIG. 2 herein. Computational models of this algorithm have already been successful. A computational test of this approach is shown in FIG. 8. Three 'true' patterns represented the saliency map for three different visual search targets. The animal's behavior was modeled as choosing the stimulus location that was the closest match to the stimulation provided by the adaptive algorithm. If this matched the target location then the trial was marked as correct (otherwise, incorrect). In such simulations, the adaptive algorithm learns stimulus patterns quickly and accurately, despite only receiving 'correct' and 'incorrect' feedback (FIG. 11, bottom). Note, once low-frequency patterns were learned, adding high-frequency components increased the complexity of stimulation patterns, finding finer patterns that better approximated the 'true' pattern (FIG. 11, top).

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. An adaptive cognitive prosthetic comprising:
a processing unit for converting input data related to a patient's visual field comprising neural activity from an input data assembly into a cognitive variable for treating visual dysfunction and selecting a stimulation pattern for conveying the cognitive variable, wherein the processing unit employs an adaptive algorithm to reduce dimensionality of the stimulation pattern via assembling the stimulation pattern by combination of subset stimulation patterns in a hierarchical format, the combination of subset stimulation patterns learned by the adaptive algorithm through error analysis comprising determining whether a combination of subset stimulation patterns meets a set or predetermined accuracy threshold guided by feedback from a behavioral paradigm and/or directly from a patient using the adaptive cognitive prosthetic;
wherein the adaptive algorithm includes discrete cosine transforms to estimate the subset stimulation patterns, and wherein frequency of the discrete cosine transforms increases with increasing complexity of the subset stimulation patterns; and
a stimulation assembly for administering the selected stimulation pattern to treat the visual dysfunction.

2. The adaptive cognitive prosthetic of claim 1, wherein the hierarchical format classifies the subset stimulation patterns according to the pattern complexity, the pattern complexity being proportional to signal frequencies defining the subset stimulation pattern.

3. The adaptive cognitive prosthetic of claim 2, wherein the subset stimulation patterns are combined in order of increasing complexity.

4. The adaptive cognitive prosthetic of claim 1, wherein the input assembly comprises a recording assembly comprising electrodes for recording the neural activity input data.

5. The adaptive cognitive prosthetic of claim 1, wherein the stimulation assembly comprises electrode arrays for administering the selected stimulation pattern via electrical discharge.

6. The adaptive cognitive prosthetic of claim 1, wherein the stimulation assembly comprises waveguides for administering the stimulation pattern via electromagnetic stimulation.

7. The adaptive cognitive prosthetic of claim 6, wherein the waveguides are provided as arrays.

8. The adaptive cognitive prosthetic of claim 1, wherein the stimulation assembly administers the selected stimulation pattern via fluctuating magnetic fields.

9. The adaptive cognitive prosthetic of claim 1, wherein the visual dysfunction comprises hemispatial neglect, and the cognitive variable corresponds to visual identification of objects in an affected region of the visual field.

10. A method of providing a stimulation pattern for conveying a cognitive variable for treating visual dysfunction comprising:
providing input data related to a patient's visual field comprising neural activity to a processing unit from an input data assembly;

converting the input data into the cognitive variable for treating visual dysfunction with the processing unit and selecting a stimulation pattern for conveying the cognitive variable with the processing unit, wherein the processing unit employs an adaptive algorithm to reduce dimensionality of the stimulation pattern via assembling the stimulation pattern by combination of subset stimulation patterns in a hierarchical format, the combination of subset stimulation patterns learned by the adaptive algorithm through error analysis comprising determining whether a combination of subset stimulation patterns meets a set or predetermined accuracy threshold guided by feedback from a behavioral paradigm and/or directly from a patient using the adaptive cognitive prosthetic;

wherein the adaptive algorithm includes discrete cosine transforms to estimate the subset stimulation patterns, and wherein frequency of the discrete cosine transforms increases with increasing complexity of the subset stimulation patterns; and administering the selected stimulation pattern with a stimulation assembly.

11. The method of claim 10, wherein the hierarchical format classifies the subset stimulation patterns according to the pattern complexity, the pattern complexity being proportional to signal frequencies defining the subset stimulation pattern.

12. The method of claim 11, wherein the subset stimulation patterns are combined in order of increasing complexity.

13. The method of claim 10, wherein the error function evaluates accuracy of each combination of subset stimulation patterns in representing one or more functions of the cognitive variable.

14. The method of claim 10, wherein the visual dysfunction comprises hemispatial neglect, and the cognitive variable corresponds to visual identification of objects in an affected region of the visual field.

* * * * *